United States Patent
Fukumoto et al.

(10) Patent No.: US 7,038,059 B2
(45) Date of Patent: May 2, 2006

(54) PROCESS FOR PREPARATION OF 4-N-SUBSTITUTED AMINO-2-AZA-1-OXABICYCLO[3.3.0] OCT-2-ENE-6-CARBOXYLIC ACID ESTERS AND PROCESS FOR PREPARATION OF THEIR INTERMEDIATES

(75) Inventors: Takashi Fukumoto, Niigata (JP); Masahiro Torihara, Niigata (JP); Yoshin Tamai, Niigata (JP)

(73) Assignee: Kuraray Co., Ltd., Kurashiki (JP)

( * ) Notice: Subject to any disclaimer, the term of this patent is extended or adjusted under 35 U.S.C. 154(b) by 110 days.

(21) Appl. No.: 10/399,047

(22) PCT Filed: Oct. 1, 2001

(86) PCT No.: PCT/JP01/08627

§ 371 (c)(1),
(2), (4) Date: Apr. 18, 2003

(87) PCT Pub. No.: WO02/32885

PCT Pub. Date: Apr. 25, 2002

(65) Prior Publication Data
US 2004/0121482 A1 Jun. 24, 2004

(30) Foreign Application Priority Data
Oct. 18, 2000 (JP) .............................. 2000-317718
Dec. 5, 2000 (JP) .............................. 2000-369723
Jan. 16, 2001 (JP) .............................. 2001-007210

(51) Int. Cl.
C07D 261/20 (2006.01)

(52) U.S. Cl. ................................................ 548/241

(58) Field of Classification Search ................ 548/241
See application file for complete search history.

(56) References Cited

FOREIGN PATENT DOCUMENTS

| EP | 424064 | 4/1991 |
|---|---|---|
| EP | 590685 | 4/1994 |
| WO | 93/17020 | 9/1993 |
| WO | 99/33781 | 7/1999 |

OTHER PUBLICATIONS

Chand et al., Journal of Medicinal Chemistry, 2001, 44(25): 4379-4392.*
Y. Sudhakar Babu, et al., "BCX-1812 (RWJ-270201): Discovery of a Novel, Highly Potent, Orally Active, and Selective Influenza Neuraminidase Inhibitor through Structure-Based Drug Design", Journal of Medicinal Chemistry, vol. 43, No. 19, XP-002333586, Aug. 31, 2000, pp. 3482-3486.
Mohamed Ikbal, et al., "Synthesis of the two enantiomers of the carbocyclic analog of nicotinamide ribose and analysis of their biological properties", Eur. J. Med. Chem., vol. 24, XP-002333587, 1989, pp. 415-420.

* cited by examiner

*Primary Examiner*—Taofiq Solola
*Assistant Examiner*—Robert Shiao
(74) *Attorney, Agent, or Firm*—Oblon, Spivak, McClelland, Maier & Neustadt, P.C.

(57) ABSTRACT

4-N-substituted amino-2-aza-1-oxabicyclo[3.3.0]oct-2-ene-6-carboxylic acid esters are produced by adding a Brønsted acid to a mixture of a 2-azabicyclo[2.2.1]hept-5-en-3-one and an alcohol, thereby causing these components to react with each other to give a salt of cis-4-amino-2-cyclopentene-1-carboxylic acid ester, then allowing the salt of cis-4-amino-2-cyclopentene-1-carboxylic acid ester thus obtained to react with an amino-protecting group introducing compound in the presence of a base, thereby giving cis-4-N-substituted amino-2-cyclopentene-1-carboxylic acid ester, and then allowing this cis-4-N-substituted amino-2-cyclopentene-1-carboxylic acid ester to react with a hypohalogenite and an aldoxime.

2 Claims, No Drawings

PROCESS FOR PREPARATION OF 4-N-SUBSTITUTED AMINO-2-AZA-1-OXABICYCLO[3.3.0] OCT-2-ENE-6-CARBOXYLIC ACID ESTERS AND PROCESS FOR PREPARATION OF THEIR INTERMEDIATES

TECHNICAL FIELD

This invention relates to a process for producing a 4-N-substituted amino-2-aza-1-oxabicyclo[3.3.0]oct-2-ene-6-carboxylic acid ester, and a process for producing an intermediate thereof.

BACKGROUND ART

4-N-substituted amino-2-aza-1-oxabicyclo[3.3.0]oct-2-ene-6-carboxylic acid ester represented General Formula (11):

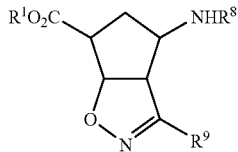

(11)

wherein $R^1$ represents an alkyl group, a cycloalkyl group, an alkenyl group, an alkynyl group, an aryl group which may be substituted or an aralkyl group which may be substituted; $R^8$ represents an amino-protecting group selected from among an alkyl group, a cycloalkyl group, an alkenyl group, an alkynyl group, an aryl group which may be substituted, an aralkyl group which may be substituted, an acyl group or an alkoxycarbonyl group; and $R^9$ represents an alkyl group which may be substituted, a cycloalkyl group, an alkenyl group, an alkynyl group, an aryl group which may be substituted, an aralkyl group which may be substituted, an acyl group or a carbamoyl group, is useful as an intermediate in the synthesis of drugs such as anti-influenza drugs (see WO99/33781 Gazette).

Conventional processes for producing 4-N-substituted amino-2-aza-1-oxabicyclo[3.3.0]oct-2-ene-6-carboxylic acid esters include (i) a process in which cis-4-N-substituted amino-2-cyclopentene-1-carboxylic acid ester represented by Formula (9):

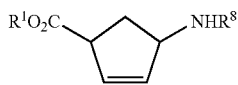

(9)

wherein $R^1$ and $R^8$ are defined as above, is reacted with a nitro compound and phenyl isocyanate (see WO99/33781 Gazette), and (ii) a process in which a cis-4-N-substituted amino-2-cyclopentene-1-carboxylic acid ester of Formula (9) is reacted with an aldoxime, N-chlorosuccinimide and a base (see WO99/33781 Gazette).

These processes both have drawbacks, however, in that they require a difficult after-treatment in order to isolate the target compound, and process (i) involves the use of phenyl isocyanate, which is unstable in water and difficult to handle, while process (ii) involves the use of relatively expensive N-chlorosuccinimide. These problems make these processes unsuited to industrial applications.

Also, a methyl ester encompassed by the raw material cis-4-N-substituted amino-2-cyclopentene-1-carboxylic acid ester represented by Formula (9) is produced by allowing a methanol solution of hydrogen chloride to react with the 2-azabicyclo[2.2.1]hept-5-en-3-one of Formula (1) (i.e., by conducting methanolysis of the 2-azabicyclo[2.2.1]hept-5-en-3-one of Formula (1)):

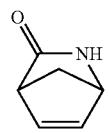

(1)

then removing the methanol, recrystallizing the residue with ether to form cis-4-amino-2-cyclopentene-1-carboxylic acid methyl ester hydrochloride, and then allowing this to react with a base and an amino-protecting group introducing compound (protectant) (see WO99/33781 Gazette).

In this process, however, a methanol solution of hydrogen chloride is prepared in advance, and the bicyclic compound of Formula (1) is added to and reacted with this solution, so there are various drawbacks, eg., (i) the solubility of hydrogen chloride in methanol is low, so a large quantity of methanol must be used, and the volumetric efficiency of the reactor is poor, and (ii) the hydrogen chloride, which theoretically only needs to be used in an amount of 1 equivalent, is used in an amount of 2 or more equivalents in order to make the reaction proceed more quickly. Consequently, this process is unsatisfactory for the purposes of industrial-scale production.

Also, the cis-4-N-substituted amino-2-cyclopentene-1-carboxylic acid ester of Formula (9) is such that the carbon atoms in the one and four positions of the cyclopentene ring are asymmetric carbons, and there are therefore compounds represented by Formula (9a) of (1S, 4R) absolute configuration, or by Formula (9b) of (1R, 4S) absolute configuration:

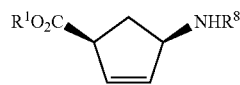

(9a)

(9b)

wherein $R^1$ and $R^8$ are defined as above.

These compounds are all useful as intermediate raw materials for pharmaceuticals and so forth, in particular, the carboxylic acid esters of Formula (9a) are known to be useful as a raw material in the synthesis of BCX-1812 (3-[1-(acetylamino)-2-ethylbutyl]-4-[(aminoiminomethyl)-amino]-2-hydroxycyclopentanecarboxylic acid), which is promising as an anti-influenza drug.

The methyl esters encompassed by these optically active carboxylic acid esters of Formula (9a) or (9b) have been conventionally produced by using a microorganism or enzyme to resolve (±)-2-azabicyclo[2.2.1]hept-5-en-3-one to obtain the optically active 2-azabicyclo[2.2.1]hept-5-en-3-one of Formula (1), subjecting this compound to methanolysis to prepare an optically active cis-4-amino-2-cyclopentene-1-carboxylic acid methyl ester, and then reacting this with a base and an amino-protecting group introducing compound (protectant) (see WO99/33781 Gazette). However, special microorganisms or enzymes must be used in the optical resolution of the optically active 2-azabicyclo[2.2.1]hept-5-en-3-one of Formula (1), and because the reaction substrate concentration was low, the reactor efficiency was also low, and the reaction time was long, among other problems. Accordingly, an optically active 2-azabicyclo[2.2.1]hept-5-en-3-one cannot be easily obtained, and as a result, this conventional process cannot be considered industrially advantageous for the production of optically active cis-4-amino-2-cyclopentene-1-carboxylic acid esters.

It is an object of the present invention to provide a process that allows the industrially advantageous production of 4-N-substituted amino-2-aza-1-oxabicyclo[3.3.0]oct-2-ene-6-carboxylic acid esters, and particularly optically active forms thereof, and to provide a process that allows the industrially advantageous production of salts of cis-4-amino-2-cyclopentene-1-carboxylic acid ester that is a raw material in the production of 4-N-substituted amino-2-aza-1-oxabicyclo[3.3.0]oct-2-ene-6-carboxylic acid esters.

DISCLOSURE OF THE INVENTION

The inventors accomplished the following present invention that achieves the stated object upon discovering that ① salts of cis-4-amino-2-cyclopentene-1-carboxylic acid ester can be efficiently obtained if, in the methanolysis of the 2-azabicyclo[2.2.1]hept-5-en-3-one of Formula (1), the compound of Formula (1) is dissolved in an alcohol such as methanol, and a Brønsted acid such as hydrogen chloride is added to this solution, rather than the compound of Formula (1) being put into a solution in which a Brønsted acid has already been dissolved in an alcohol, ② 4-N-substituted amino-2-aza-1-oxabicyclo[3.3.0]oct-2-ene-6-carboxylic acid esters of Formula (11) can be simply obtained by desalting salts of cis-4-amino-2-cyclopentene-1-carboxylic acid ester with a base, protecting the amino groups, and then reacting with a hypohalogenite and a specific aldoxime, and ③ optically active cis-4-amino-2-cyclopentene-1-carboxylic acid esters can be obtained by reacting an optically active specific carboxylic acid or sulfonic acid used as an optical resolution agent with a compound obtained by desalting salts of cis-4-amino-2-cyclopentene-1-carboxylic acid ester with a base.

Specifically, the present invention provides a process for producing 4-N-substituted amino-2-aza-1-oxabicyclo[3.3.0]oct-2-ene-6-carboxylic acid ester represented by General Formula (11):

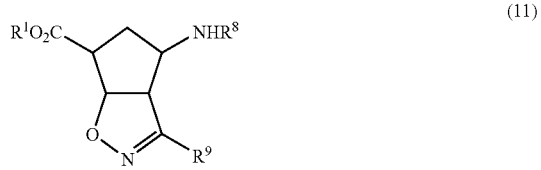

(11)

wherein $R^1$ represents an alkyl group, a cycloalkyl group, an alkenyl group, an alkynyl group, an aryl group which may be substituted or an aralkyl group which may be substituted; $R^8$ represents an amino-protecting group introduced by an amino-protecting group introducing compound and selected from among an alkyl group, a cycloalkyl group, an alkenyl group, an alkynyl group, an aryl group which may be substituted, an aralkyl group which may be substituted, an acyl group or alkoxycarbonyl group; and $R^9$ represents an alkyl group which may be substituted, a cycloalkyl group, an alkenyl group, an alkynyl group, an aryl group which may be substituted, an aralkyl group which may be substituted, an acyl group or a carbamoyl group, comprising:

the step of adding a Brønsted acid represented by Formula (3):

HX (3)

wherein X represents a halogen atom, a carboxylic acid residue, a sulfonic acid residue or a phosphoric acid residue, to a mixture of a 2-azabicyclo[2.2.1]hept-5-en-3-one represented by Formula (1):

(1)

and an alcohol represented by Formula (2):

$R^1OH$ (2)

wherein $R^1$ is defined as above, thereby causing these components to react with each other to form a salt of cis-4-amino-2-cyclopentene-1-carboxylic acid ester represented by Formula (4):

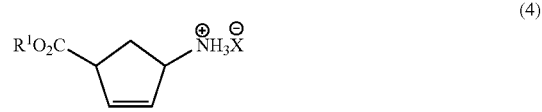

(4)

wherein $R^1$ and X are defined as above;

the step of allowing the salt of cis-4-amino-2-cyclopentene-1-carboxylic acid ester thus obtained to react with the amino-protecting group introducing compound in the presence of a base to form cis-4-N-substituted amino-2-cyclopentene-1-carboxylic acid ester represented by Formula (9):

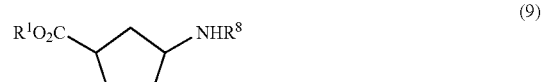

(9)

wherein $R^1$ and $R^8$ are defined as above; and the step of allowing the cis-4-N-substituted amino-2-cyclopentene-1-carboxylic acid ester thus obtained to react with a hypohalogenite and an aldoxime represented by Formula (10):

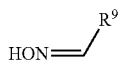
(10)

wherein $R^9$ is defined as above.

The present invention also provides a process for producing the salts of cis-4-amino-2-cyclopentene-1-carboxylic acid ester of Formula (4), comprising:

the step of adding the Brønsted acid of Formula (3) to a mixture of the 2-azabicyclo[2.2.1]hept-5-en-3-one of Formula (1) and the alcohol of Formula (2), so that these components react with each other. In this case it is preferable for the reaction to be conducted in a hydrocarbon solvent.

The present invention also provides a process for producing the 4-N-substituted amino-2-aza-1-oxabicyclo[3.3.0] oct-2-ene-6-carboxylic acid ester of Formula (11), comprising:

the step of allowing the cis-4-N-substituted amino-2-cyclopentene-1-carboxylic acid ester of Formula (9) to react with a hypohalogenite and the aldoxime of Formula (10).

The present invention also provides a process for producing a salt of optically active cis-4-amino-2-cyclopentene-1-carboxylic acid ester represented by Formula (8a) or (8b):

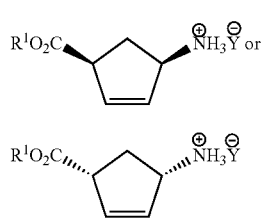

wherein $R^1$ is defined as above; and the Y anion is a carboxylic acid ion of Formula (6) or a sulfonic acid ion of Formula (7), comprising:

the step of allowing a cis-4-amino-2-cyclopentene-1-carboxylic acid ester represented by Formula (5):

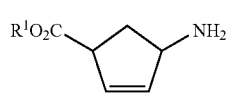

(5)

wherein $R^1$ is defined as above, to react in the presence of a solvent with, as an optical resolution agent, an optically active 2-hydroxycarboxylic acid represented by Formula (6):

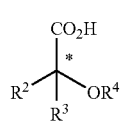

(6)

wherein "*" represents an asymmetric carbon atom; $R^2$ and $R^3$ each independently represents a hydrogen atom, an alkyl group, an alkenyl group, an alkynyl group, an aryl group which may be substituted or an aralkyl group which may be substituted or may form a ring together with the carbon atom to which they are bonded; and $R^4$ represents a hydrogen atom, an alkyl group, an alkenyl group, an alkynyl group, an acyl group, an aryl group which may be substituted or an aralkyl group which may be substituted, or an optically active sulfonic acid represented by Formula (7):

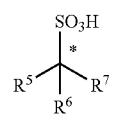

(7)

wherein "*" represents an asymmetric carbon atom; $R^5$, $R^6$ and $R^7$ each independently represents a hydrogen atom, an alkyl group, a cycloalkyl group, a bicycloalkyl group, an alkenyl group, an alkynyl group, an alkoxyl group, an aryl group which may be substituted or an aralkyl group which may be substituted or may form a ring together with the carbon atom to which they are bonded, or two of $R^5$, $R^6$ and $R^7$ may form a ring together with the carbon atom to which they are bonded.

It is preferable here that the cis-4-amino-2-cyclopentene-1-carboxylic acid ester represented by Formula (5) to be used is synthesized according to the step of adding the Brønsted acid of Formula (3) to a mixture of the 2-azabicyclo[2.2.1]hept-5-en-3-one of Formula (1) and the alcohol of Formula (2), thereby causing these components to react with each other to form the salt of cis-4-amino-2-cyclopentene-1-carboxylic acid ester of Formula (4), and the step of allowing the salt of cis-4-amino-2-cyclopentene-1-carboxylic acid ester thus obtained to react with a base.

The present invention also provides a process for producing an optically active 4-N-substituted amino-2-aza-1-oxabicyclo[3.3.0]oct-2-ene-6-carboxylic acid ester represented by Formula (11a):

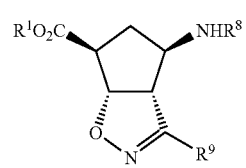

(11a)

wherein $R^1$, $R^8$ and $R^9$ are defined as above, comprising:

the step of allowing the salt of optically active cis-4-amino-2-cyclopentene-1-carboxylic acid ester of Formula (8a) to react with an amino-protecting group introducing compound in the presence of a base to form the optically active cis-4-N-substituted amino-2-cyclopentene-1-carboxylic acid ester represented by Formula (9a):

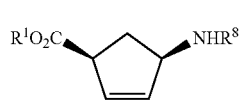

(9a)

wherein $R^1$ and $R^8$ are defined as above; and the step of allowing the optically active cis-4-N-substituted amino-2-cyclopentene-1-carboxylic acid ester thus obtained to react with a hypohalogenite and the aldoxime of Formula (10).

BEST MODE FOR CARRYING OUT THE INVENTION

Schemes 1 and 2 below represent the basic concepts of the producing process of the present invention.

Scheme 1

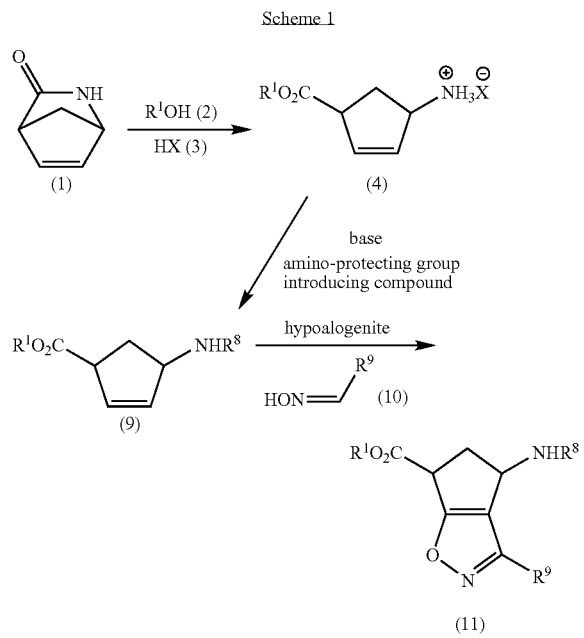

Scheme 2

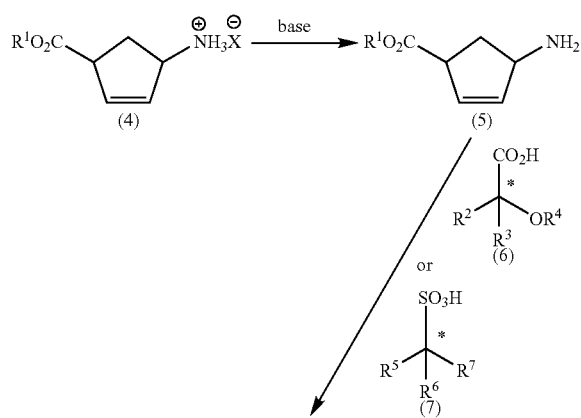

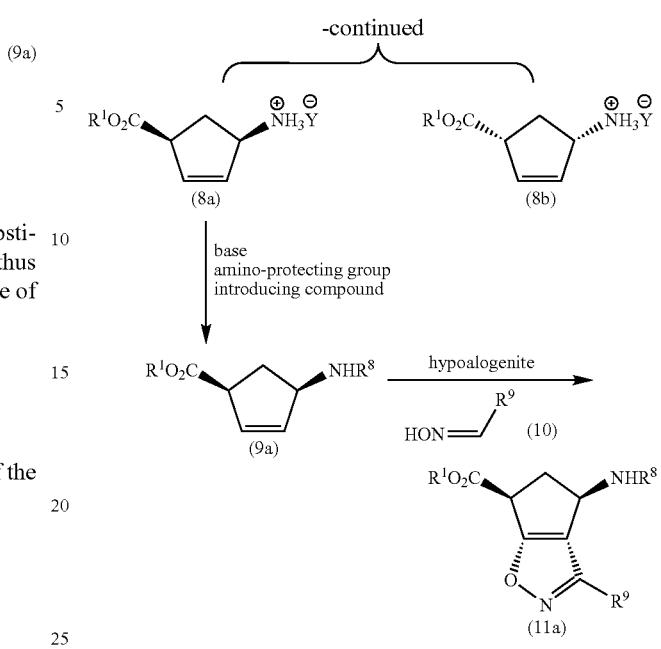

The present invention will now be described through reference to the various steps in these schemes.

Any substituents labeled the same in Schemes 1 and 2 have the same meaning.

Scheme 1 Producing route of (1)→(4)→(9)→(11)

First, we will describe a process for producing the compound of Formula (11) using the compound of Formula (1) as a raw material and going from the compound of Formula (4) through the compound of Formula (9).

The producing step from the compound of Formula (1) to the compound of Formula (4) is useful as a process for producing the compound of Formula (4), which is an intermediate of the compound of Formula (1). Also, the producing step from the compound of Formula (9) to the compound of Formula (11) is useful as a process for producing the compound of Formula (11).

Producing Step from Compound of Formula (1) to Compound of Formula (4)

First, the Brønsted acid of Formula (3) is added to a mixture of the 2-azabicyclo[2.2.1]hept-5-en-3-one of Formula (1) and the alcohol of Formula (2), thereby subjecting the compound of Formula (1) to alcoholysis and obtaining the salt of cis-4-amino-2-cyclopentene-1-carboxylic acid ester of Formula (4).

Examples of the alkyl group represented by $R^1$ in the alcohol of Formula (2) include methyl group, ethyl group, n-propyl group, i-propyl group, n-butyl group, 2-butyl group, 2-ethyl-1-butyl group, 3-pentyl group, 4-heptyl group, and the like; examples of the cycloalkyl group include cyclopropyl group, cyclopentyl group, cyclohexyl group, and the like; examples of the alkenyl group include vinyl group, allyl group, 1-propenyl group, and the like; and examples of the alkynyl group include ethynyl group, 2-propynyl group, and the like. Examples of the aryl group include phenyl group, naphthyl group, and the like, and examples of the aralkyl group include benzyl group, phenethyl group, and the like. The aromatic ring of the aryl group and the aralkyl group may have substituents, and examples of such substituents include a halogen atom such as chlorine atom, bromine atom, iodine atom, and the like; an alkyl group such as methyl group, ethyl group, n-propyl group, and the like; an aryl group such as naphthyl group, p-methylphenyl group, and the like; an alkoxy group such as methoxy group, ethoxy group, n-propoxy group, and the like; nitro group.

Specific favorable examples of the alcohol of Formula (2) having $R^1$ defined as above include methanol, ethanol, 1-propanol, 2-propanol, 1-butanol, cyclohexanol, benzyl alcohol, and the like.

Examples of the halogen atom represented by X in the Brønsted acid of Formula (3) include fluorine atom, chlorine atom, bromine atom, iodine atom, and the like; examples of the carboxylic acid residue include acetic acid residue, propionic acid residue, oxalic acid residue, formic acid residue, mandelic acid residue, and the like; and examples of the sulfonic acid residue include p-toluenesulfonic acid residue, methanesulfonic acid residue, trifluoromethanesulfonic acid residue, camphor-sulfonic acid residue, sulfuric acid residue, and the like.

Specific favorable examples of the Brønsted acid of Formula (3) having X defined as above include hydrogen chloride, hydrogen bromide, sulfuric acid, phosphoric acid, acetic acid, formic acid, alkanesulfonic acid, and the like. Of these, hydrogen chloride, sulfuric acid and alkanesulfonic acid are particularly favorable.

The amount of the alcohol of Formula (2) used in this alcoholysis reaction generally is preferably between 1.0 and 100 mol per mole of the 2-azabicyclo[2.2.1]hept-5-en-3-one of Formula (1), and from the standpoints of cost and ease of after-treatment, a range of 1.0 to 10 mol is more preferable, and a range of 1.0 to 3.0 mol is particularly favorable. When the alcohol of Formula (2) functions doubly as a reaction solvent, it may be used in an amount over the above range.

The amount of the Brønsted acid of Formula (3) used generally is preferably between 1.0 and 10 mol per mole of the 2-azabicyclo[2.2.1]hept-5-en-3-one of Formula (1), and from the standpoints of cost and ease of after-treatment, a range of 1.0 to 3.0 mol is more preferable.

This alcoholysis reaction is preferably carried out in the presence of a solvent. The solvent is preferably used simultaneously with the alcohol of Formula (2).

There are no particular restrictions on this solvent as long as it does not impede the reaction, but examples include toluene, xylene, mesitylene, and other aromatic hydrocarbons; hexane, heptane, octane, and other aliphatic hydrocarbons; and methylene chloride, chloroform, dichloroethane, and other chlorinated hydrocarbons; and the like. When one of these hydrocarbon solvents is used, the target product will precipitate from the reaction mixture as the reaction proceeds, which facilitates after-treatment. These solvents may be used singly or in mixture of two or more types. The amount of the solvent used is preferably from 1 to 100 times by weight with respect to the 2-azabicyclo [2.2.1]hept-5-en-3-one of Formula (1), and from the standpoints of cost and ease of after-treatment, a range of 1 to 20 times by weight is more preferable.

The reaction temperature during this alcoholysis reaction is preferably between −20 and 70° C., and from the standpoints of reaction velocity and the stability of the target product, a range of −10 to 50° C. is more preferable. The reaction time may vary with the reaction temperature and other factors, but a range of 0.5 to 20 hours is favorable.

The salt of cis-4-amino-2-cyclopentene-1-carboxylic acid ester of Formula (4) obtained from the above reaction can be easily isolated from the reaction mixture by filtering off the crystals when the salt precipitates in the form of crystals from the reaction mixture, or by concentrating the reaction mixture when there is no crystal precipitation from the reaction mixture. The isolated salt of cis-4-amino-2-cyclopentene-1-carboxylic acid ester of Formula (4) can be used directly as an intermediate in the synthesis of anti-influenza drugs and other such pharmaceuticals. If needed, its purity can be further raised by refining it by some means ordinarily employed in organic synthesis, such as recrystallization, column chromatography or sublimation.

Producing Step from Compound of Formula (4) to Compound of Formula (9)

Next, in order to desalt the salt of cis-4-amino-2-cyclopentene-1-carboxylic acid ester of Formula (4) obtained by alcoholysis reaction and introduce a protecting group of the amino group, the compound of Formula (4) is reacted with an amino-protecting group introducing compound in the presence of a base, which yields the cis-4-N-substituted amino-2-cyclopentene-1-carboxylic acid ester of Formula (9).

The substituent $R^8$ in the cis-4-N-substituted amino-2-cyclopentene-1-carboxylic acid ester of Formula (9) is introduced by the amino-protecting group introducing compound, and examples of the alkyl group represented thereby include methyl group, ethyl group, n-propyl group, i-propyl group, n-butyl group, 2-butyl group, 3-pentyl group, 4-heptyl group, 2-ethyl-1-butyl group, and the like; examples of the cycloalkyl group include cyclopropyl group, cyclopentyl group, cyclohexyl group, and the like; examples of the alkenyl group include vinyl group, allyl group, 1-propenyl group, and the like; and examples of the alkynyl group include ethynyl group, 2-propynyl group, and the like. Examples of the aryl group include phenyl group, naphthyl group, and the like, and examples of the aralkyl group include benzyl group, phenethyl group, and the like. The aromatic ring of the aryl group and the aralkyl group may have substituents, and examples of such substituents include a halogen atom such as chlorine atom, bromine atom, iodine atom, and the like; an alkyl group such as methyl group, ethyl group, n-propyl group, and the like; an aryl group such as naphthyl group, p-methylphenyl group, and the like; an alkoxy group such as methoxy group, ethoxy group, n-propoxy group, and the like; and nitro group. Examples of the acyl group include acetyl group, propionyl group, and the like, and examples of the alkoxycarbonyl group include tert-butoxycarbonyl group, benzyloxycarbonyl group, and the like.

Specific examples of the amino-protecting group introducing compound having $R^8$ defined as above include methyl iodide, ethyl iodide, propyl iodide, methyl bromide, ethyl bromide, propyl bromide, methyl chloride, ethyl chloride, propyl chloride, and other alkyl halides; acetic anhydride, propionic anhydride, benzoic anhydride, and other acid anhydrides; acetyl chloride, benzoyl chloride, acetyl bromide, benzoyl bromide, and other acid halides; methoxycarbonyl chloride, ethoxycarbonyl chloride, tert-butoxycarbonyl chloride, cyclohexyloxycarbonyl chloride, phenyloxycarbonyl chloride, benzyloxycarbonyl chloride, and other alkoxycarbonyl chlorides; and dimethyl dicarbonate, diethyl dicarbonate, and other dialkyl dicarbonates.

Sodium hydrogencarbonate, potassium hydrogencarbonate, lithium hydrogencarbonate, sodium carbonate, potassium carbonate, lithium carbonate, sodium hydroxide, potassium hydroxide, lithium hydroxide, and other such inorganic bases, or triethylamine, pyridine, diisopropylethylamine, and other such organic bases can be used as the base in the desalting reaction and the amino-protecting group introduction reaction.

The amount of the base used is preferably 0.5 to 5.0 mol per mole of the salt of cis-4-amino-2-cyclopentene-1-carboxylic acid ester of Formula (4), and from the standpoints of cost and ease of after-treatment, a range of 0.5 to 3.0 mol is more preferable.

The desalting and amino-protecting group introducing reactions are preferably carried out in the presence of a solvent.

There are no particular restrictions on this solvent as long as it does not impede the reaction, and examples include toluene, xylene, mesitylene, and other aromatic hydrocarbons; methanol, ethanol, isopropanol, and other alcohols; ethyl acetate, propyl acetate, butyl acetate, and other esters; hexane, heptane, octane, and other aliphatic hydrocarbons; methylene chloride, dichloroethane, dichlorobenzene, and other halogenated hydrocarbons; and diethyl ether, diisopropyl ether, 1-butyl methyl ether, tetrahydrofuran, and other ethers.

The amount of the solvent used is preferably 0.5 to 100 times by weight with respect to the salt of cis-4-amino-2-cyclopentene-1-carboxylic acid ester of Formula (4), and from the standpoints of cost and ease of after-treatment, a range of 0.5 to 30 times by weight is more preferable.

The reaction temperature during the desalting and amino-protecting group introducing reactions is preferably between −20 and 120° C., and from the standpoints of reaction velocity and the stability of the target product, a range of −5 to 100° C. is more preferable. The reaction time may vary with the reaction temperature and other factors, but a range of 0.5 to 40 hours is preferable.

When tert-butyl dicarbonate is used as the amino-protecting group introducing compound, tert-butoxycarbonyl group can be introduced to the amino groups at the four position, when acetic anhydride is used, acetyl group can be introduced, and when methyl iodide is used, methyl group can be introduced.

The cis-4-N-substituted amino-2-cyclopentene-1-carboxylic acid ester of Formula (9) obtained from the above reaction can be easily isolated from the reaction mixture by filtering off the crystals when the ester precipitates in the form of crystals from the reaction mixture, or by concentrating the reaction mixture when there is no crystal precipitation from the reaction mixture. The isolated cis-4-N-substituted amino-2-cyclopentene-1-carboxylic acid ester of Formula (9) can be used directly as an intermediate in the synthesis of anti-influenza drugs and other such pharmaceuticals. If needed, its purity can be further raised by refining it by some means ordinarily employed in organic synthesis, such as recrystallization, column chromatography or sublimation.

Producing Step from Compound of Formula (9) to Compound of Formula (11)

The 4-N-substituted amino-2-aza-1-oxabicyclo[3.3.0]oct-2-ene-6-carboxylic acid ester of Formula (11) can be obtained by reacting the cis-4-N-substituted amino-2-cyclopentene-1-carboxylic acid ester of Formula (9) obtained above with a hypohalogenite and the aldoxime of Formula (10).

Examples of the alkyl group represented by $R^9$ in the aldoxime of Formula (10) include methyl group, ethyl group, n-propyl group, i-propyl group, n-butyl group, 2-butyl group, 3-pentyl group, 4-heptyl group, 2-ethyl-1-butyl group, and the like. These alkyl groups may have substituents, and examples of such substituents include a halogen atom such as chlorine atom, bromine atom, iodine atoms, and the like; an alkoxy group such as methoxy group, ethoxy group, n-propoxy group, and the like; and a nitro group. Examples of the cycloalkyl group include cyclopropyl group, cyclopentyl group, cyclohexyl group, and the like; examples of the alkenyl group include vinyl group, allyl group, 1-propenyl group, and the like; examples of the alkynyl group include ethynyl group, 2-propynyl group, and the like; examples of the aryl group include phenyl group, naphthyl group, and the like, and examples of the aralkyl group include benzyl group, phenethyl group, and the like. The aromatic ring of the aryl group and the aralkyl group may have substituents, and examples of such substituents include a halogen atom such as chlorine atom, bromine atom, iodine atom, and the like; an alkyl group such as methyl group, ethyl group, n-propyl group, and the like; an aryl group such as naphthyl group, p-methylphenyl group, and the like; an alkoxy group such as methoxy group, ethoxy group, n-propoxy group, and the like; and nitro group. Examples of the acyl group include acetyl group, propionyl group, and the like, and examples of the carbamoyl group include N,N-dimethylcarbamoyl group, N-methylcarbamoyl group, and the like.

The aldoxime of Formula (10) having $R^9$ defined as above can be obtained by mixing a corresponding aldehyde with an aqueous hydroxylamine solution, and can be used in this producing process.

The amount of the aldoxime of Formula (10) used is preferably from 1.0 to 10.0 times (molar) with respect to the cis-4-N-substituted amino-2-cyclopentene-1-carboxylic acid ester of Formula (9), and from the standpoints of cost and ease of after-treatment, a range of 1.0 to 4.0 times (molar) is more preferable.

Examples of the hypohalogenite include sodium hypochlorite, potassium hypochlorite, calcium hypochlorite, ammonium hypochlorite, sodium hypobromite, potassium hypobromite, and the like. These hypohalogenites are preferably used in the form of an aqueous solution.

The amount of the hypohalogenite used is preferably from 0.5 to 10.0 times (molar) with respect to the cis-4-N-substituted amino-2-cyclopentene-1-carboxylic acid ester of Formula (9), and from the standpoints of cost and ease of after-treatment, a range of 0.5 to 5.0 times (molar) is more preferable.

The reaction between the cis-4-N-substituted amino-2-cyclopentene-1-carboxylic acid ester of Formula (9) and the aldoxime of Formula (10) is preferably conducted in the presence of a solvent. There are no particular restrictions on this solvent as long as it does not impede the reaction, and examples include water; hexane, heptane, octane, and other aliphatic hydrocarbons; toluene, xylene, cymene, and other aromatic hydrocarbons; methanol, ethanol, isopropanol, tert-butanol, and other alcohols; methyl acetate, ethyl acetate, propyl acetate, and other esters; and methylene chloride, dichloroethane, and other halogenated hydrocarbons. These solvents may be used singly or in mixture of two or more types.

The amount of the solvent used is preferably from 0.5 to 100 times by weight with respect to the cis-4-N-substituted amino-2-cyclopentene-1-carboxylic acid ester of Formula (9), and from the standpoints of cost and ease of after-treatment, a range of 0.5 to 30 times by weight is more preferable.

The temperature in the reaction between the cis-4-N-substituted amino-2-cyclopentene-1-carboxylic acid ester of Formula (9) and the aldoxime of Formula (10) usually is preferably between −20 and 120° C., and a range of −5 to 100° C. is more preferable. The reaction time may vary with the reaction temperature, the type of raw material and other factors, but a range of 0.5 to 40 hours is favorable.

There are no particular restrictions on the procedure or operating process for the reaction between the cis-4-N-substituted amino-2-cyclopentene-1-carboxylic acid ester of Formula (9) and the aldoxime of Formula (10), and the reaction may be conducted by batch or in a continuous process. For instance, the cis-4-N-substituted amino-2-cyclopentene-1-carboxylic acid ester of Formula (9), the aldoxime of Formula (10), and, if needed, a solvent can be mixed, and a solution of the hypohalogenite can be added dropwise to the mixture.

When the 4-N-substituted amino-2-aza-1-oxabicyclo[3.3.0]oct-2-ene-6-carboxylic acid ester of Formula (11) obtained from the above reaction precipitates as crystals in the reaction mixture during the reaction, this ester can be easily isolated by filtering off these crystals, or upon completion of the reaction, the reaction mixture can be extracted with an organic solvent such as hexane, heptane, toluene or methylene chloride, and this ester can be isolated by concentrating the resulting organic layer. This product can be used directly as an intermediate in the synthesis of anti-influenza drugs and other pharmaceuticals. If needed, its purity can be further raised by refining it by some means ordinarily employed in organic synthesis, such as recrystallization, column chromatography or sublimation.

Scheme 2 Producing Route of (4)→(5)→(8a (8b))→(9a)→(11a)

First, we will describe a process for producing the compound of Formula (11a), using the compound of Formula (4) obtained from the compound of Formula (1) as a raw material, going from the compound of Formula (4) through the compound of Formula (5), separating the compound of Formula (8a) or (8b) by optical resolution, converting the compound of Formula (8a) into the compound of Formula (9a) that retains its optical activity, and converting the compound of Formula (9a) into the compound of Formula (11a).

The producing step of optical resolution from the compound of Formula (5) to the compound of Formula (8a) or (8b) is useful as a process for producing the compound of Formula (8a), which is an intermediate of the compound of Formula (11a). Similarly, the producing route from the compound of Formula (1) to the compound of Formula (4) to the compound of Formula (5) to the compound of Formula (8a) or (8b) is also useful as a process for producing the compound of Formula (8a). Further, the producing route from the compound of Formula (8a) to the compound of Formula (9a) to the compound of Formula (11a) is useful as a process for producing the optically active compound of Formula (11).

Producing Step from Compound of Formula (1) to Compound of Formula (4)

This producing step is the same as that described for Scheme 1.

Producing Step from Compound of Formula (4) to Compound of Formula (5)

The salt of cis-4-amino-2-cyclopentene-1-carboxylic acid ester of Formula (4) is reacted with a base to obtain the cis-4-amino-2-cyclopentene-1-carboxylic acid ester of Formula (5).

Except for the fact that no amino-protecting group introducing compound is used, the reaction conditions here can be the same as those in the production of the compound of Formula (9) from the compound of Formula (4) in Scheme 1.

Producing Step from Compound of Formula (5) to Compound of Formula (8a) or (8b)

The salt of optically active cis-4-amino-2-cyclopentene-1-carboxylic acid ester of Formula (8a) or (8b) is produced by reacting the cis-4-amino-2-cyclopentene-1-carboxylic acid ester of Formula (5) with an optically active 2-hydroxycarboxylic acid represented by Formula (6) or an optically active sulfonic acid represented by Formula (7) as an optical resolution agent in the presence of a solvent.

Examples of the alkyl group represented by $R^2$, $R^3$, $R^4$, $R^5$, $R^6$ and $R^7$ in Formulas (6) and (7) include methyl group, ethyl group, n-propyl group, i-propyl group, n-butyl group, and the like; examples of the alkenyl group include vinyl group, allyl group, 1-propenyl group, and the like; examples of the alkynyl group include ethynyl group, 2-propynyl group, and the like; examples of the aryl group include phenyl group, naphthyl group, and the like; and examples of the aralkyl group include benzyl group, phenethyl group, and the like. The aromatic ring of the aryl group and the aralkyl group may have substituents, and examples of such substituents include a halogen atom such as chlorine atom, bromine atom, iodine atom, and the like; an alkyl group such as methyl group, ethyl group, n-propyl group, and the like; an aryl group such as naphthyl group, p-methylphenyl group, and the like; an alkoxy group such as methoxy group, ethoxy group, n-propoxy group, and the like; and a nitro group.

Examples of the ring that may be formed by $R^2$ and $R^3$ and the carbon atom to which they are bonded include cyclohexane ring, cyclopentane ring, and the like.

Examples of the cycloalkyl groups represented by $R^5$, $R^6$ and $R^7$ include cyclohexyl group, cyclopentyl group, cyclopropyl group, and the like; examples of the bicycloalkyl groups represented by $R^5$, $R^6$ and $R^7$ include 7,7-dimethyl-bicyclo[2.2.1]heptan-2-on-1-yl group, isopinocampheyl group, and the like; and examples of the alkoxy group include methoxy group, ethoxy group, n-propoxy group, and the like. Examples of the ring that may be formed by $R^5$, $R^6$ and $R^7$ and the carbon atoms to which they are bonded include 7,7-dimethylbicyclo[2.2.1]heptane ring, norbornane ring, and the like; and examples of the ring that may be formed by two of $R^5$, $R^6$ and $R^7$ and the carbon atom to which they are bonded include cyclohexane ring, cyclopentane ring, and the like.

Examples of the acyl group represented by $R^4$ include formyl group, acetyl group, propionyl group, benzoyl group, and the like.

Specific examples of the optically active 2-hydroxycarboxylic acid of Formula (6) having $R^2$, $R^3$ and $R^4$ defined as above include (R)-mandelic acid, (S)-mandelic acid, (R)-2-hydroxybutanoic acid, (S)-2-hydroxybutanoic acid, (R)-2-hydroxypentanoic acid, (S)-2-hydroxypentanoic acid, and the like; and specific examples of the optically active sulfonic acid of Formula (7) having $R^5$, $R^6$ and $R^7$ include camphorsulfonic acid, (R)-phenylethanesulfonic acid, (S)-phenylethanesulfonic acid, and the like.

The Y anion in the compound of Formula (8a) or (8b) is a carboxylic acid anion of the optically active 2-hydroxycarboxylic acid of Formula (6) or a sulfonic acid anion of the sulfonic acid of Formula (7).

The amount of the optically active 2-hydroxycarboxylic acid of Formula (6) or the optically active sulfonic acid of Formula (7) used is preferably from 0.3 to 1.5 times (molar)

with respect to the cis-4-amino-2-cyclopentene-1-carboxylic acid ester of Formula (5), and from the standpoints of cost and ease of after-treatment, a range of 0.4 to 1.0 times (molar) is more preferable.

There are no particular restrictions on the solvent used in this optical resolution reaction as long as it has no adverse effect on the reaction, and any solvent used in ordinary organic reactions can be used. Examples of a favorable solvent include methanol, ethanol, n-propanol, i-propanol, and other alcohols; acetonitrile, propionitrile, benzonitrile, and other nitrites; toluene, xylene, cumene and other aromatic hydrocarbons; and acetone, methyl ethyl ketone, methyl isopropyl ketone, and other ketones. These solvents may be used singly or in mixture of two or more types. The amount of the solvent used is preferably from 1 to 50 times by weight with respect to the cis-4-amino-2-cyclopentene-1-carboxylic acid ester of Formula (5), and a range of 1 to 10 times by weight is more preferable from the standpoint of cost.

The reaction temperature in this optical resolution reaction may vary with the substrate used, the type of solvent and other factors, but a range of room temperature to 120° C. is favorable, and a range of 25 to 70° C. is preferred. The reaction time may also vary with the substrate used, the type of solvent and other factors, but a range of about 5 minutes to 5 hours is favorable, and a range of about 5 minutes to 2 hours is preferable.

When the optically active 2-hydroxycarboxylic acid of Formula (6) or the optically active sulfonic acid of Formula (7) used as an optical resolution agent in this optical resolution reaction is an (R) isomer, a salt of [(1S, 4R)-cis-4-amino-2-cyclopentene-1-carboxylic acid ester.(R)-optical resolution agent] and a salt of [(1R, 4S)-cis-4-amino-2-cyclopentene-1-carboxylic acid ester.(R)-optical resolution agent] is obtained corresponding to a (1S, 4R)-cis-4-amino-2-cyclopentene-1-carboxylic acid ester and a (1R, 4S)-cis-4-amino-2-cyclopentene-1-carboxylic acid ester, while when the optically active 2-hydroxycarboxylic acid of Formula (6) or the optically active sulfonic acid of Formula (7) used is an (S) isomer, a salt of [(1S, 4R)-cis-4-amino-2-cyclopentene-1-carboxylic acid ester.(S)-optical resolution agent] and a salt of [(1R, 4S)-cis-4-amino-2-cyclopentene-1-carboxylic acid ester.(S)-optical resolution agent] is obtained.

The diastereomer salts obtained in this manner can be optically separated from one another by, for example, cooling the reaction solution to the crystallization temperature until a supersaturated state exists, and utilizing the difference in solubility between the diastereomer salts with respect to a solvent to preferentially crystallize the diastereomer salt with the lower solubility. The crystallization temperature may vary with the type and amount of solvent used, the reaction temperature and other factors, but from the standpoint of cost, a range of −10° C. to 30° C. is preferable.

When one of the diastereomer salts is being crystallized, it is preferable for a small amount of diastereomer salt to be crystallized to add as seed crystals to the reaction solution. The precipitated diastereomer salt can be isolated by a standard process such as filtration or centrifuging.

The obtained diastereomer salts, for example, can be subjected to reaction of triethylamine, sodium hydroxide, potassium hydroxide or another such base, and thereby converted into the (1S, 4R)-cis-4-amino-2-cyclopentene-1-carboxylic acid ester of Formula (8a) or the (1R, 4S)-cis-4-amino-2-cyclopentene-1-carboxylic acid ester of Formula (8b). This operation can also be omitted, and the diastereomer salts used directly as an intermediate in the synthesis of anti-influenza drugs and other such pharmaceuticals.

Producing Step from Compound of Formula (8a) to Compound of Formula (9a)

Next, the optically active cis-4-N-substituted amino-2-cyclopentene-1-carboxylic acid ester represented by Formula (9a) is obtained by reacting the salt of optically active cis-4-amino-2-cyclopentene-1-carboxylic acid ester of Formula (8a) with an amino-protecting group introducing compound in the presence of a base.

This producing step can be performed in the same manner as the producing step from the compound of Formula (4) to the compound of Formula (9) in Scheme 1.

Producing Step from Compound of Formula (9a) to Compound of Formula (11a)

Next, the optically active 4-N-substituted amino-2-aza-1-oxabicyclo[3.3.0]oct-2-ene-6-carboxylic acid ester represented by Formula (11a) is obtained by reacting the optically active cis-4-N-substituted amino-2-cyclopentene-1-carboxylic acid ester of Formula (9a) obtained above with a hypohalogenite and the aldoxime of Formula (10).

This producing step can be performed in the same manner as the producing step from the compound of Formula (9) to the compound of Formula (11) in Scheme 1.

If the optically active 4-N-substituted amino-2-aza-1-oxabicyclo[3.3.0]oct-2-ene-6-carboxylic acid ester of Formula (11a) obtained from the above reaction precipitates as crystals in the reaction mixture during the reaction, this ester can be easily isolated by filtering off these crystals, or upon completion of the reaction, the reaction mixture can be extracted with an organic solvent such as hexane, heptane, toluene or methylene chloride, and this ester can be isolated by concentrating the resulting organic layer. This product can be used directly as an intermediate in the synthesis of anti-influenza drugs and other pharmaceuticals. If needed, its purity can be further raised by refining it by some means ordinarily employed in organic synthesis, such as recrystallization or column chromatography.

EXAMPLES

The present invention will now be described in specific terms through examples, but is not limited by these examples.

Example 1

20.0 g (183.3 mmol) of 2-azabicyclo[2.2.1]hept-5-en-3-one, 8.8 g (274.7 mmol) of methanol, and 150 mL of toluene were put into a four-necked flask (300 mL volume) equipped with a hydrogen chloride introducing tube, a thermometer, and an exhaust tube. 6.7 g (183.8 mmol) of hydrogen chloride was introduced into the obtained mixture over a period of 2 hours through the hydrogen chloride introducing tube at room temperature. Following 1 hour of stirring, the precipitated crystals were filtered off with a glass filter. The obtained crystals were dried under reduced pressure to give 30.8 g (173.2 mmol) of cis-4-amino-2-cyclopentene-1-carboxylic acid methyl ester hydrochloride (that is, (1S*, 4R*)-4-amino-1-methoxycarbonyl-2-cyclopentene hydrochloride). The yield was 94.4%.

Example 2

20.0 g (183.3 mmol) of 2-azabicyclo[2.2.1]hept-5-en-3-one and 40.0 g (1248.6 mmol) of methanol were put into a four-necked flask (300 mL volume) equipped with a hydrogen chloride introducing tube, a thermometer and an exhaust tube. 6.7 g (183.8 mmol) of hydrogen chloride was introduced into the obtained mixture over a period of 2 hours through the hydrogen chloride introducing tube at room temperature. Following 1 hour of stirring, the reaction mixture was analyzed by internal standard process by high performance liquid chromatography (HPLC), which revealed that 31.0 g (174.5 mmol) of cis-4-amino-2-cyclopentene-1-carboxylic acid methyl ester hydrochloride was produced. The yield was 94.9%.

Example 3

20.0 g (183.3 mmol) of 2-azabicyclo[2.2.1]hept-5-en-3-one and 40.0 g (1248.6 mmol) of methanol were put into a four-necked flask (300 mL volume) equipped with a thermometer. 18.0 g (183.5 mmol) of concentrated sulfuric acid was introduced into the obtained mixture over a period of 2 hours at room temperature. Following 1 hour of stirring, the reaction mixture was analyzed by internal standard process by high performance liquid chromatography (HPLC), which revealed that 37.6 g (157.2 mmol) of cis-4-amino-2-cyclopentene-1-carboxylic acid methyl ester hydrogen sulfate was produced. The yield was 85.8%.

Comparative Example 1

20.0 g (183.3 mmol) of 2-azabicyclo[2.2.1]hept-5-en-3-one and 400 mL (400 mmol) of a 1N-hydrogen chloride methanol solution were put into a four-necked flask (500 mL volume) equipped with a thermometer, and the mixture was heated and refluxed for 10 hours. The obtained reaction mixture was concentrated under reduced pressure. The residue was dissolved in 27 mL of diethyl ether, and then cooled to 5° C. The precipitated crystals were filtered off using a glass filter. The obtained crystals were dried under reduced pressure to give 25.6 g (144.1 mmol) of cis-4-amino-2-cyclopentene-1-carboxylic acid methyl ester hydrochloride. The yield was 78.6%.

Example 4

17.7 g (0.100 mol) of cis-4-amino-2-cyclopentene-1-carboxylic acid methyl ester hydrochloride, 22.9 g (0.105 mol) of di-tert-butyl dicarbonate, 5.6 g (0.053 mol) of sodium carbonate and 70 mL of heptane were put into a four-necked flask (300 mL volume) and equipped with a thermometer. While this mixture was stirred, 100 mL of water was added, and then the mixture was stirred for 3 hours at room temperature. The organic layer separated after the stirring was stopped. The solvent was distilled off from the organic layer under reduced pressure to give 23.9 g (0.099 mol) of cis-4-tert-butoxycarbonylamino-2-cyclopentene-1-carboxylic acid methyl ester. The yield was 99%.

Example 5

29.0 g (120 mmol) of cis-4-tert-butoxycarbonylamino-2-cyclopentene-1-carboxylic acid methyl ester, 27.5 g (239 mmol) of 2-ethylbutylaldoxime and 120 mL of heptane were put into a three-necked flask (500 mL volume) equipped with a thermometer and a dropping funnel. After the mixture was cooled to 3° C., 217.5 g (275 mmol) of an aqueous 9.4% sodium hypochlorite solution was added dropwise through the dropping funnel over a period of 1 hour. Upon completion of dropping, the reaction mixture was stirred for 6 hours. The precipitated crystals were filtered off under suction. The obtained crystals were dried under reduced pressure to give 33.0 g (90.3 mmol) of (3aR*, 4R*, 6S*, 6aS*)-2-aza-4-tert-butoxycarbonylamino-3-(1'-ethylpropyl)-1-oxabicyclo[3.3.0]oct-2-ene-6-carboxylic acid methyl ester with a purity of 97%. The mother liquor contained 3.0 g (8 mmol) of (3aR*, 4R*, 6S*, 6aS*)-2-aza-4-tert-butoxycarbonylamino-3-(1'-ethylpropyl)-1-oxabicyclo[3.3.0]oct-2-ene-6-carboxylic acid methyl ester, so the yield, combined with the ester obtained in the form of crystals, was 81.9%.

Example 6

Except for changing the reaction temperature to 50° C., the same operation as in Example 5 was carried out. This yielded 34 g (95.9 mmol) of (3aR*, 4R*, 6S*, 6aS*)-2-aza-4-tert-butoxycarbonylamino-3-(1'-ethylpropyl)-1-oxabicyclo[3.3.0]oct-2-en-6-carboxylic acid methyl ester. The yield was 79.9%.

Example 7

200 g (1.13 mol) of cis-4-amino-2-cyclopentene-1-carboxylic acid methyl ester hydrochloride, 540 g of acetonitrile and 60 g of methanol were put into a four-necked flask (1 L volume) equipped with a thermometer and a stirrer. After the mixture was raised to 50° C., 98.4 g (0.57 mol) of sodium (R)-mandelate was added over a period of 30 minutes. After the mixture was stirred for 30 minutes, the solids thus produced were filtered off with a glass filter. The filtrate was gradually cooled to 3° C. while being stirred, and the precipitated crystal of (1S, 4R)-4-amino-2-cyclopentene-1-carboxylic acid methyl ester.(R)-mandelate was filtered off. The obtained crystal was analyzed by high performance liquid chromatography (HPLC), which revealed the optical purity to be 92.1% ee. The weight of crystal after dried was 82.6 g (0.28 mol) and the yield was 24.8% (based on racemic modification).

Example 8

200 g (1.13 mol) of cis-4-amino-2-cyclopentene-1-carboxylic acid methyl ester hydrochloride, 540 g of acetonitrile 60 g of methanol and 85.7 g (0.57 mol) of (R)-mandelic acid were put into a four-necked flask (1 L volume) equipped with a thermometer and a stirrer. After the mixture was raised to 50° C., 57.0 g (0.57 mol) of triethylamine was added over a period of 30 minutes. The mixture was stirred for 30 minutes, and then gradually cooled to 3° C. while being stirred, after which the precipitated crystal of (1S, 4R)-4-amino-2-cyclopentene-1-carboxylic acid methyl ester.(R)-mandelate was filtered off. The obtained crystal was analyzed by HPLC, which revealed the optical purity to be 92.3% ee. The weight of crystal after dried was 81.9 g (0.28 mol) and the yield was 24.8% (based on racemic modification).

Example 9

Except for using 98.4 g (0.57 mol) of sodium (S)-mandelate instead of 98.4 g (0.57 mol) of sodium (R)-mandelate, the same operation as in Example 7 was carried out. The obtained crystal of (1R, 4S)-4-amino-2-cyclopentene-1-carboxylic acid methyl ester.(S)-mandelate was analyzed by HPLC, which revealed the optical purity to be 91.8% ee. The weight of crystal after dried was 83.6 g (0.29 mol) and the yield was 25.7% (based on racemic modification).

Example 10

Except for using 85.7 g (0.57 mol) of (S)-mandelic acid instead of 85.7 g (0.57 mol) of (R)-mandelic acid, the same operation as in Example 8 was carried out. The obtained crystal of (1R, 4S)-4-amino-2-cyclopentene-1-carboxylic acid methyl ester.(S)-mandelate was analyzed by HPLC, which revealed the optical purity to be 92.8% ee. The weight of crystal after dried was 83.3 g (0.28 mol) and the yield was 24.8% (based on racemic modification).

Example 11

Except for using 144.9 g (0.57 mol) of sodium (S)-camphorsulfonate instead of 98.4 g (0.57 mol) of sodium (R)-mandelate, the same operation as in Example 7 was carried out. The obtained crystal of (1S, 4R)-4-amino-2-cyclopentene-1-carboxylic acid methyl ester.(S)-camphorsulfonate was analyzed by HPLC, which revealed the optical purity to be 65.5% ee. The weight of crystal after dried was 33.6 g (0.09 mol) and the yield was 8.0% (based on racemic modification).

Example 12

Except for using 142.7 g (0.57 mol) of (S)-camphorsulfonate monohydrate instead of 85.7 g (0.57 mol) of (R)-mandelic acid, the same operation as in Example 8 was carried out. The obtained crystal of (1S, 4R)-4-amino-2-cyclopentene-1-carboxylic acid methyl ester.(S)-camphorsulfonate was analyzed by HPLC, which revealed the optical purity to be 72.8% ee. The weight of crystal after dried was 41.1 g (0.11 mol) and the yield was 9.7% (based on racemic modification).

Example 13

29.1 g (0.100 mol) of (1S, 4R)-4-amino-2-cyclopentene-1-carboxylic acid methyl ester.(R)-mandelate, 22.9 g (0.105 mol) of di-tert-butyl dicarbonate, 5.6 g (0.053 mol) of sodium carbonate and 70 mL of heptane were put into a four-necked flask (300 mL volume) equipped with a thermometer. While this mixture was stirred, 100 mL of water was added, and then the mixture was stirred for 3 hours at 50° C. The organic layer was separated after the stirred was stopped. The solvent was distilled off from the organic layer under reduced pressure to give 23.4 g (0.097 mol) of (1S, 4R)-4-tert-butoxycarbonylamino-2-cyclopentene-1-carboxylic acid methyl ester. The yield was 97%.

Example 14

Except for using 29.0 g (120 mmol) of (1S, 4R)-4-tert-butoxycarbonylamino-2-cyclopentene-1-carboxylic acid methyl ester instead of 29.0 g (120 mmol) of cis-4-tert-butoxycarbonylamino-2-cyclopentene-1-carboxylic acid methyl ester, the same operation as in Example 5 was carried out. 35 g (98.7 mmol) of (3aR, 4R, 6S, 6aS)-2-aza-4-tert-butoxycarbonylamino-3-(1'-ethylpropyl)-1-oxabicyclo[3.3.0]oct-2-ene-6-carboxylic acid methyl ester was obtained. The yield was 82.2%.

INDUSTRIAL APPLICATION

According to the present invention, a salt of a cis-4-amino-2-cyclopentene-1-carboxylic acid ester can be produced at high yield and low cost, simply, and in an industrially advantageous manner. Further, 4-N-substituted amino-2-aza-1-oxabicyclo[3.3.0]oct-2-en-6-carboxylic acid ester can be produced from the above carboxylic acid ester inexpensively, simply and in an industrially advantageous manner.

Also, according to the present invention, (1S, 4R)-4-amino-1-carboalkoxy-2-cyclopentene or (1R, 4S)-4-amino-1-carboalkoxy-2-cyclopentene can be produced at high purity, high yield and simply, and optically active 4-N-substituted amino-2-aza-1-oxabicyclo[3.3.0]oct-2-ene-6-carboxylic acid ester can be produced from these.

What is claimed is:

1. A process for producing a 4-N-substituted amino-2-aza-1-oxabicyclo[3.3.0]oct-2-ene-6-carboxylic acid ester represented by General Formula (11):

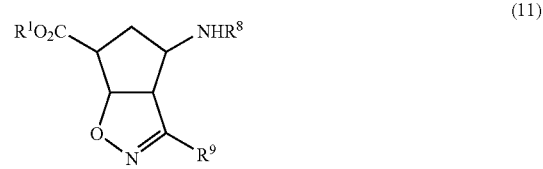

wherein $R^1$ represents an alkyl group, a cycloalkyl group, an alkenyl group, an alkynyl group, an aryl group which may be substituted or an aralkyl group which may be substituted; $R^8$ represents an amino-protecting group introduced by an amino-protecting group introducing compound and selected from among an alkyl group, a cycloalkyl group, an alkenyl group, an alkynyl group, an aryl group which may be substituted, an aralkyl group which may be substituted, an acyl group or an alkoxycarbonyl group; and $R^9$ represents an alkyl group which may be substituted, a cycloalkyl group, an alkenyl group, an alkynyl group, an aryl group which may be substituted, an aralkyl group which may be substituted, an acyl group or a carbamoyl group, comprising:

the step of adding a Brønsted acid represented by Formula (3):

wherein X represents a halogen atom, a carboxylic acid residue, a sulfonic acid residue or a phosphoric acid residue, to a mixture of a 2-azabicyclo[2.2.1]hept-5-en-3-one represented by Formula (1):

and an alcohol represented by Formula (2):

wherein $R^1$ is defined as above, thereby causing these components to react with each other to form a salt of cis-4-amino-2-cyclopentene-1-carboxylic acid ester represented by Formula (4):

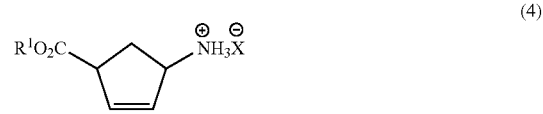

wherein $R^1$ and X are defined as above;

the step of allowing the salt of cis-4-amino-2-cyclo-pentene-1-carboxylic acid ester thus obtained to react with the amino-protecting group introducing compound in the presence of a base to form a cis-4-N-substituted amino-2-cyclopentene-1-carboxylic acid ester represented by Formula (9):

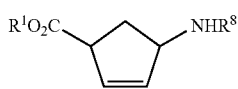
(9)

wherein $R^1$ and $R^8$ are defined as above; and the step of allowing the cis-4-N-substituted amino-2-cyclopentene-1-carboxylic acid ester thus obtained to react with a hypohalogenite and an aldoxime represented by Formula (10):

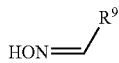
(10)

wherein $R^9$ is defined as above.

2. A process for producing a 4-N-substituted amino-2-aza-1-oxabicyclo[3.3.0]oct-2-ene-6-carboxylic acid ester represented by Formula (11):

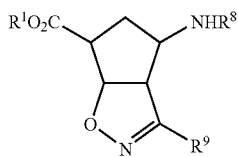
(11)

wherein $R^1$ represents an alkyl group, a cycloalkyl group, an alkenyl group, an alkynyl group, an aryl group which may be substituted or an aralkyl group which may be substituted; $R^8$ represents an amino-protecting group selected from among an alkyl group, a cycloalkyl group, an alkenyl group, an alkynyl group, an aryl group which may be substituted, an aralkyl group which may be substituted, an acyl group or an alkoxycarbonyl group; and $R^9$ represents an alkyl group which may be substituted, a cycloalkyl group, an alkenyl group, an alkynyl group, an aryl group which may be substituted, an aralkyl group which may be substituted, an acyl group or a carbamoyl group, comprising:

the step of allowing cis-4-N-substituted amino-2-cyclopentene-1-carboxylic acid ester represented by Formula (9):

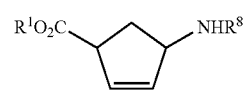
(9)

wherein $R^1$ and $R^8$ are defined as above, to react with a hypohalogenite and an aldoxime represented by Formula (10):

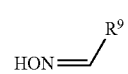
(10)

wherein $R^9$ is defined as above.

* * * * *